United States Patent
Nantz et al.

[11] Patent Number: 5,869,715
[45] Date of Patent: Feb. 9, 1999

[54] POLYFUNCTIONAL CATIONIC CYTOFECTINS

[75] Inventors: Michael H. Nantz; Michael J. Bennett; Rajiv P. Balasubramaniam, all of Davis, Calif.

[73] Assignee: The Reagents of the University of California, Oakland, Calif.

[21] Appl. No.: 534,471

[22] Filed: Sep. 27, 1995

[51] Int. Cl.$^6$ ................................................. C07C 101/00
[52] U.S. Cl. .................... 554/110; 554/103; 554/109; 554/231; 554/108; 564/291; 564/292; 564/293; 568/583; 568/589
[58] Field of Search .................................. 554/103, 108, 554/110, 109, 231; 564/291, 292, 293; 568/583, 589

[56] References Cited

U.S. PATENT DOCUMENTS

| | | |
|---|---|---|
| 4,812,449 | 3/1989 | Rideout . |
| 5,171,678 | 12/1992 | Behr et al. . |
| 5,186,923 | 2/1993 | Piwnica-Worms et al. . |
| 5,208,036 | 5/1993 | Eppstein et al. . |
| 5,264,618 | 11/1993 | Felgner et al. . |
| 5,277,897 | 1/1994 | Piwnica-Worms et al. . |
| 5,279,833 | 1/1994 | Rose . |
| 5,334,761 | 8/1994 | Gebeyehu ................................ 564/197 |

FOREIGN PATENT DOCUMENTS 9413362  6/1995  WIPO .

OTHER PUBLICATIONS

A Flexible Approach to Synthetic Lipid Ammonium Salts for Polynucleotide Transfection by Bennett et al., Tetrahedron Letters, vol. 36, No. 13, pp. 2207–2210, 1995.

Primary Examiner—Gary Geist
Assistant Examiner—Deborah D Carr
Attorney, Agent, or Firm—James M. Ritchey

[57] ABSTRACT

For use in transporting biologically active species into and through membrane barriers, a cationic amine compound is utilized that has the general structure:

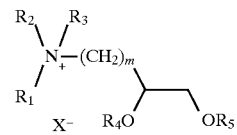

wherein $R_4$ and $R_5$ are a pair of same or different lipoyl moieties selected from a group consisting of an alkyl, alkenyl, alkynyl, alkanoyl, alkenoyl, or alkynoyl groups and for $R_1$ $R_2$, and $R_3$ at least two are hydroxylated, ether containing, or acyloxy containing alkyl, alkenyl, or alkynyl groups or at least one amine bonded halogen containing moiety selected from a group consisting of a halogenated alkyl, alkenyl, or alkynyl group or a mixture of at least one halogen containing moiety selected from a group consisting of a halogenated alkyl, alkenyl, or alkynyl group and at least one hydroxylated, ether containing, or acyloxy containing alkyl, alkenyl, or alkynyl group, and $X^-$ is an anion.

4 Claims, 3 Drawing Sheets

POLYFUNCTIONAL CATIONIC CYTOFECTINS

BACKGROUND OF THE INVENTION

1. Field of the Invention

Provided is a collection of cytofectins or cationic lipids that bind and transport polynucleotides, polypeptides, pharmaceutical substances and other biologically active species through membrane barriers. More specifically, cationic lipids are disclosed that complex with selected molecular species and facilitate delivery of those selected species into and through membranes and comparable boundary structures.

2. Description of the Background Art

Cellular transfection strategies for gene therapy and similar goals have been designed and performed, but many of these procedures involve recombinant virus vectors and various problems exist with these viral gene transfer systems. Even generally advantageous adenovirus techniques encounter difficulties since most humans have antibodies to many of the adenovirus serogroups, including those that have been chosen as vectors. Wild type adenoviral superinfection of an adenoviral vector treated patient may result in propagating the recombinant vector as a defective viral particle, with the ability to infect many unintended individuals (if chosen to have a rare serogroup). The chance of adenoviral contamination is quite low but not impossible. The safety of using these genetic materials in humans remains unclear and thus hazardous.

Safe, non-viral vector methods for transfection or gene therapy are essential. A few such lipid delivery systems for transporting DNA, proteins, and other chemical materials across membrane boundaries have been synthesized by research groups and business entities. Most of the synthesis schemes are relatively complex and generate lipid based delivery systems having only limited transfection abilities. A need exists in the field of gene therapy for cationic lipid species that have a high biopolymer transport efficiency. It has been known for some time that a very limited number of certain quaternary ammonium derivatized (cationic) liposomes spontaneously associate with DNA, fuse with cell membranes, and deliver the DNA into the cytoplasm and these species have been termed "cytofectins". LIPOFECTIN™ represents a first generation of cationic liposome formulation development. LIPOFECTIN™ is composed of a 1:1 formulation of the quaternary ammonium containing compound DOTMA and dioleoylphosphatidylethanolamine sonicated into small unilamellar vesicles in water. Problems associated with LIPOFECTIN™ include non-metabolizable ether bonds, inhibition of protein kinase C activity, and direct cytotoxicity. In response to these problems, a number of other related compounds have been developed. The monoammonium compounds of the subject invention improve upon the capabilities of existing cationic liposomes and serve as a very efficient delivery system for biologically active chemicals.

As indicated immediately above, various cationic lipids have been synthesized in previous references. For example, U.S. Pat. No. 4,812,449 discloses in situ active compound assembly of biologically active agents at target locations in preference to surroundings which are desired to be unaffected. Several charged and uncharged amine derivatives are described.

Introduced in U.S. Pat. No. 5,171,678 are lipopolyamines and their use for transfecting eukaryotic cells. A polynucleotide is mixed with the subject lipopolyamine and contacted with the cells to be treated.

U.S. Pat. Nos. 5,186,923 and 5,277,897 relate an enhancement of cellular accumulation of lipophilic cationic organometallic compounds by reduction of the intramembrane potential. Technetium containing compounds are disclosed.

Lipophilic cationic compounds are presented in U.S. Pat. No. 5,208,036. Asymmetrical amine compounds are synthesized and employed in a method for DNA transfection. The amines are quaternized by two hydrogens or alkyl, aryl, aralkyl, quinuclidino, piperidino, pyrrolidino, or morpholine groups, unlike the present invention.

U.S. Pat. No. 5,264,618 discloses cationic lipids for intracellular delivery of biologically active molecules. Asymmetric ammonium containing cationic lipids are presented for transporting molecules into membrane enclosed systems. The amines are quaternized by two hydrogens or alkyl groups, unlike the present invention.

Transfection of nucleic acids into animal cells via a neutral lipid and a cationic lipid is revealed in U.S. Pat. No. 5,279,833. Liposomes with nucleic acid transfection activity are formed from the neutral lipid and the ammonium salt containing cationic lipid.

U.S. Pat. No. 5,334,761 describes other amine containing cationic lipids are reported. Cationic lipids are utilized to form aggregates for delivery of macromolecules and other compounds into cells. The amines are quaternized by two hydrogens or unbranched alkyl groups, unlike the present invention.

In the PCT publication of PCT/US94/13362 a heterocyclic diamine is disclosed. A symmetrical quaternary diamine having lipid tails is related for forming liposomes.

The foregoing patents and publication reflect the state of the art of which the applicants are aware and are tendered with the view toward discharging applicants' acknowledged duty of candor in disclosing information which may be pertinent in the examination of this application. It is respectfully submitted, however, that none of these patents teach or render obvious, singly or when considered in combination, applicants' claimed invention.

SUMMARY OF THE INVENTION

An object of the present invention is to disclose a category of amines that greatly facilitate the delivery of biologically active compounds through membrane structures.

Another object of the present invention is to present a group of cationic amine compounds that assist in the transport of selected macromolecules and other substances into and past membrane barriers.

A further object of the present invention is to relate a collection of biologically active molecule transporters having the general structure:

wherein m=1–10; $R_1$, $R_2$, and $R_3$ are the same or different and are hydrogen, an alkyl group, an alkenyl group, an alkynyl group, a hydroxylated alkyl, alkenyl, or alkynyl group, an ether containing alkyl, alkenyl, or alkynyl group, or a halogenated alkyl, alkenyl, or alkynyl group; $R_4$ is an alkyl group, an alkenyl group, an alkynyl group, or an alkyl, alkenyl, or alkynyl containing acyl group; $R_5$ is an alkyl group, an alkenyl group, an alkynyl group, or an alkyl, alkenyl, or alkynyl containing acyl group; and X⁻ is an anion that assist in the transport of selected macromolecules and other substances into and past membrane barriers.

Disclosed are novel monoamine cationic transporter molecules (and one diamine derivative) that facilitate the delivery of such compounds as polynucleotides, polypeptides, and the like into and beyond membrane walls. Generally related are compounds having the structure:

wherein m=1–10; $R_1$, $R_2$, and $R_3$ are the same or different and are hydrogen, an alkyl group, an alkenyl group, an alkynyl group, a hydroxylated alkyl, alkenyl, or alkynyl group, an ether containing alkyl, alkenyl, or alkynyl group, or a halogenated alkyl, alkenyl, or alkynyl group; $R_4$ is an alkyl group, an alkenyl group, an alkynyl group, or an alkyl, alkenyl, or alkynyl containing acyl group; $R_5$ is an alkyl group, an alkenyl group, an alkynyl group, or an alkyl, alkenyl, or alkynyl containing acyl group; and X⁻ is an anion.

Other objects, advantages, and novel features of the present invention will become apparent from the detailed description that follows, when considered in conjunction with the associated drawings.

DESCRIPTION OF THE PREFERRED EMBODIMENT

Figure 1:
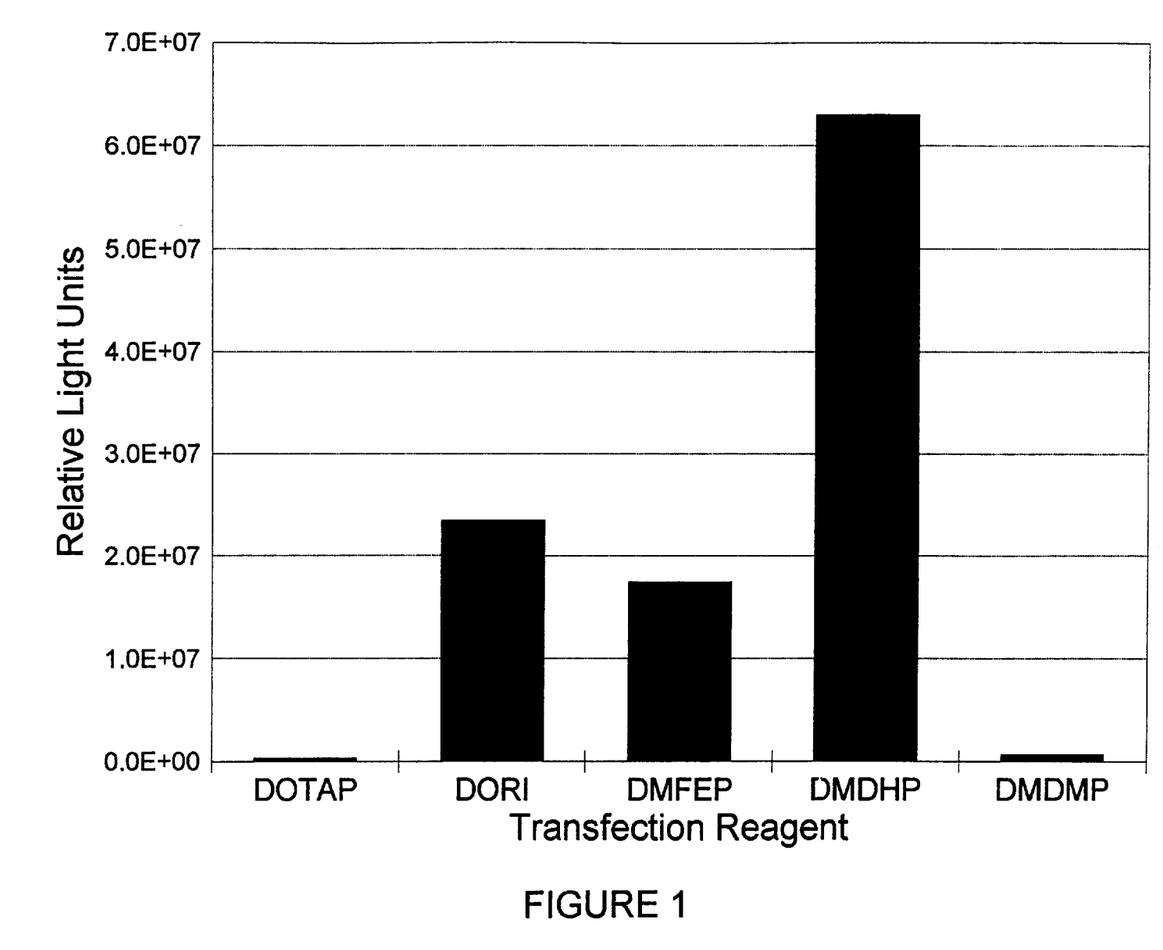
FIG. 1 shows a comparison of cytofectin-mediated DNA transfection using NIH 3T3 cells.
Figure 2:
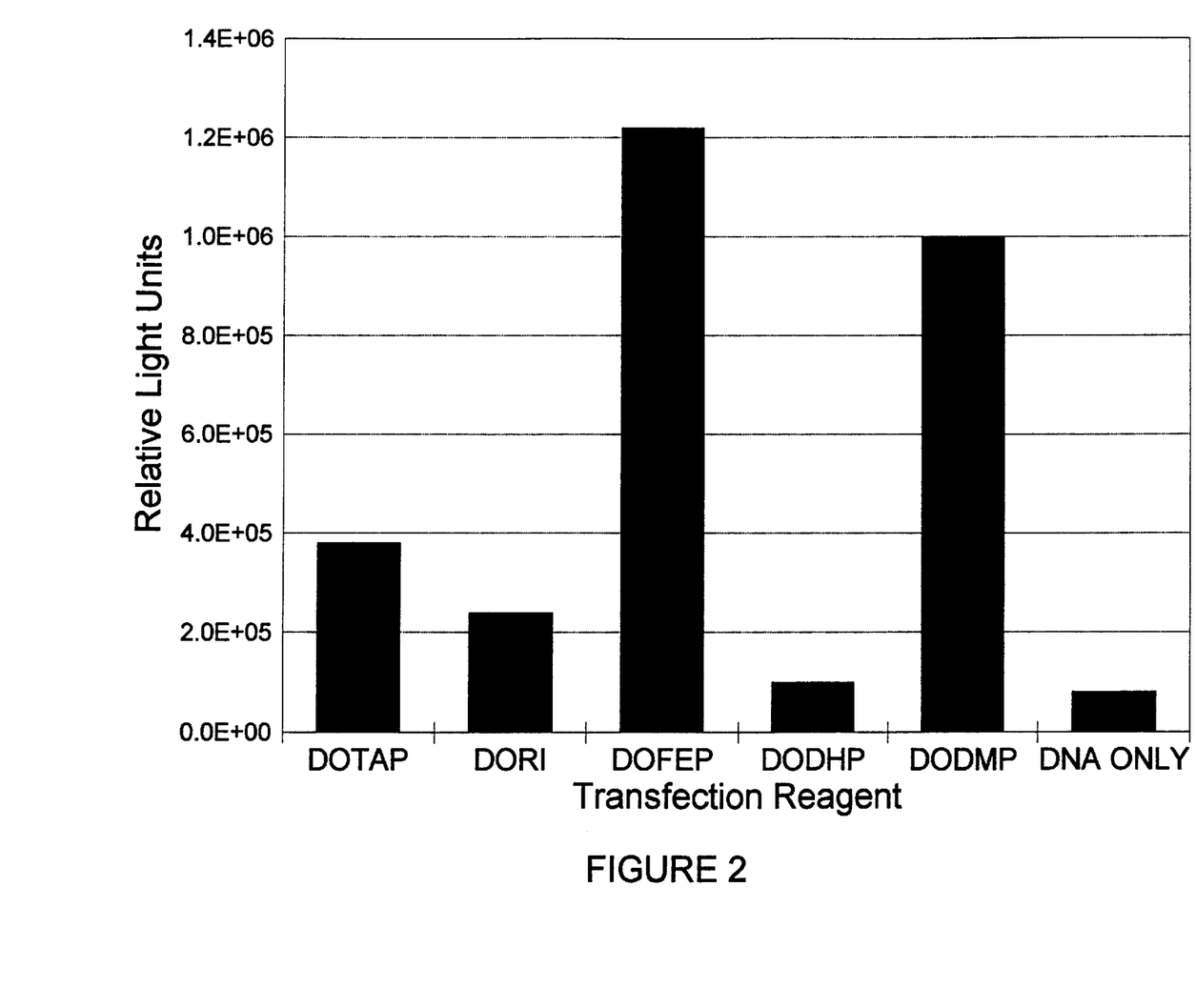
FIG. 2 presents an in vivo comparison of cytofectin-mediated DNA transfection in Balb-C mice.

Referring now to the following disclosure and to the data presented in FIGS. 1–2, there are described preferred embodiments of a cationic monoamine having at least a pair of lipoyl moieties selected from a group consisting of an alkyl chain, an alkenyl chain, and an alkyl or alkenyl containing acyl chain such as:

wherein m=1–10; $R_1$, $R_2$, and $R_3$ are the same or different and are hydrogen, an alkyl group, an alkenyl group, an alkynyl group, a hydroxylated alkyl, alkenyl, or alkynyl group, an ether containing alkyl, alkenyl, or alkynyl group, a halogenated alkyl, alkenyl, or alkynyl group, or acyl or acyloxy containing alkyl, alkenyl, or alkynyl group; $R_4$ is an alkyl group, an alkenyl group, an alkynyl group, or an alkyl, alkenyl, or alkynyl containing acyl group; $R_5$ is an alkyl group, an alkenyl group, an alkynyl group, or an alkyl, alkenyl, or alkynyl containing acyl group; and X⁻ is an anion. The extra, with m more than 1, number of methylenes is introduced by standard procedures that complement the described subject synthetic pathways.

A first preferred structure is:

wherein for Compound A: n=1–10, usually between 1 and 3, preferably 1; $R_3$ is a hydrogen, an alkyl group, an alkenyl group, an alkynyl group, or a hydroxylated alkyl, alkenyl, alkynyl group, often an alkyl group of from 1 to 10 carbons, preferably a methyl group; $R_4$ and $R_5$ are the same or different with each an alkyl group, an alkenyl group, an alkynyl group, or an alkyl, alkenyl, or alkynyl containing acyl group; and X⁻ is an anion, usually a halide, and preferably iodide.

Generalized Synthesis Scheme For Compound A

General Precursor for Compound A

Compound A where: the abbreviation Tr in the synthesis scheme denotes —C(Ph)$_3$, n=1–10, usually between 1 and 3, preferably 1; R$_3$ is a hydrogen, an alkyl group, an alkenyl group, an alkynyl group, or a hydroxylated alkyl, alkenyl, alkynyl group, often an alkyl group of from 1 to 10 carbons, preferably a methyl group; R$_4$ and R$_5$ are the same or different with each an alkyl group, an alkenyl group, an alkynyl group, or an alkyl, alkenyl, or alkynyl containing acyl group; and X$^-$ is an anion, usually a halide, and preferably iodide. It is stressed that although other procedures are contemplated to be within the realm of this disclosure, a preferred method for introducing different acyl containing R$_4$ and R$_5$ groups in this compound, and in the compounds below, is the synthesis method given in "A Flexible Approach to Synthetic Lipid Ammonium Salts for Polynucleotide Transfection" by Bennett et al. (*Tetrahedron Letters*, Vol. 36, No. 13, pp. 2207–2210) and is herein incorporated by reference. In this method an acyl migration is employed to produce the mixed ester products.

In the general synthesis scheme for Compound A derivatives, the first step involves reacting a tert-butyldiphenylsilyloxy derivatized material (made via a reaction of the dihydroxyethyl starting material with ClSiPh$_2$tBu) with (triphenylmethoxy)methyloxirane (synthesized according to the procedure described in Bennett, M. J., Malone, R. W., and Nantz, M. H. *Tetrahedron Lett.* 1995, 36, 2207) in the presence of lithium perchlorate in absolute ethanol. Diethyl ether in formic acid comprised the second step. The third step is a reaction with an alkyl, alkenyl, or alkynyl halide or an alkyl, alkenyl, or alkynyl containing acyl halide. The fourth step is tetrabutylammonium fluoride and THF initiated removal of the tert-butyldiphenylsilyloxy protection groups to produce the general precursor compound. The general precursor compound is then allowed to react with a selected alkyl, alkenyl, alkynyl or hydroxylated alkyl, alkenyl, or alkynyl halide.

Compound B wherein for Compound B: n=1–10, usually between 1 and 3, preferably 1; R$_3$ is a hydrogen, an alkyl group, an alkenyl group, an alkynyl group, or a hydroxylated alkyl, alkenyl, alkynyl group, often an alkyl group of from 1 to 10 carbons, preferably a methyl group; R$_4$ and R$_5$ are the same or different with each an alkyl group, an alkenyl group, an alkynyl group, or an alkyl, alkenyl, or alkynyl containing acyl group; R$_6$ is an alkyl group, an alkenyl group, an alkynyl group, or an acyl containing group all from 1 to 10 carbons, preferably a methyl group; R$_7$ is an alkyl group, an alkenyl group, an alkynyl group, or an acyl containing group all from 1 to 10 carbons, preferably a methyl group; and X$^-$ is an anion, usually a halide, and preferably iodide.

Generalized Synthesis Scheme For Compound B

General Precursor for Compound B

Compound B where: n=1–10, usually between 1 and 3, preferably 1; R$_3$ is a hydrogen, an alkyl group, an alkenyl group, an alkynyl group, or a hydroxylated alkyl, alkenyl, alkynyl group, often an alkyl group of from 1 to 10 carbons, preferably a methyl group; R$_4$ and R$_5$ are the same or different with each an alkyl group, an alkenyl group, an alkynyl group, or an alkyl, alkenyl, or alkynyl containing acyl group; R$_6$ is an alkyl group, an alkenyl group, an alkynyl group of from 1 to 10 carbons, preferably a methyl group; R$_7$ is an alkyl group, an alkenyl group, an alkynyl group of from 1 to 10 carbons, preferably a methyl group; and X$^-$ is an anion, usually a halide, and preferably iodide.

In the general synthesis scheme for Compound B the first step involves reacting an amine starting material with (triphenylmethoxy)methyloxirane in the presence of lithium perchlorate in absolute ethanol. Diethyl ether in formic acid comprised the second step. The third step is a reaction with an alkyl, alkenyl, or alkynyl halide or an alkyl, alkenyl, or alkynyl containing acyl halide. The general precursor compound is then allowed to react with a selected alkyl, alkenyl, alkynyl or hydroxylated alkyl, alkenyl, or alkynyl halide.

Compound C wherein for Compound C: a, b, or d are the same or different and are from 0–10, usually between 0 and 3, preferably 0 or 1; R$_4$ and R$_5$ are the same or different with each an alkyl group, an alkenyl group, an alkenyl group, or an alkyl, alkenyl, or alkynyl containing acyl group; $R_8$, $R_9$, or $R_{10}$ are the same or different with each an alkyl, alkenyl, or alkynyl group or halogenated alkyl, alkenyl, or alkynyl group as long as one is halogen containing; and $X^-$ is an anion, usually a halide, and preferably iodide.

More specifically for Compound C a preferred structure is:

Compound C-1 wherein for Compound C: $a=0–10$, usually between 0 and 3, preferably 1; $R_4$ and $R_5$ are the same or different with each an alkyl group, an alkenyl group, an alkynyl group, or an alkyl, alkenyl, or alkynyl containing acyl group; $R_8$ is a halogenated alkyl, alkenyl, or alkynyl group, preferably a trifluoromethyl group; $R_{11}$ and $R_{12}$ are the same or different with each an alkyl, alkenyl, or alkynyl group or halogenated alkyl, alkenyl, or alkynyl group; and $X^-$ is an anion, usually a halide, and preferably iodide.

Generalized Synthesis Scheme For Compound C-1

$R_{11}\diagdown N \diagup H$
$\quad |$
$\quad H$ a) PhCHO
b) $R_8(CH_2)$—X
c) $H_2O$
d) NaOH $R_8$—$(CH_2)_a \diagdown N \diagup H$
$\qquad\qquad\quad |$
$\qquad\qquad\quad R_{11}$ $R_8$—$(CH_2)_a \diagdown N \diagup H$
$\qquad\qquad\quad |$
$\qquad\qquad\quad R_{11}$

+

<image placeholder: epoxide with OTr>

1) $LiClO_4$, EtOH, Heat
2) $HCO_2H$ 85%, $ET_2O$
3) RC(O)Cl (2.1), DMAP
   $Et_3N$, $CH_2Cl_2$ $\qquad\qquad\quad R_8$
$\qquad\qquad\quad |$
$\qquad\qquad\quad (CH_2)_a$
$R_{11}\diagdown N \diagdown$
$\qquad\qquad\qquad\diagdown$
$\qquad\quad R_4O \quad OR_5$ General Precursor for Compound C-

Generalized Synthesis Scheme For Compound C-1

General Precursor for Compound C-1 $\xrightarrow{R_{12}X}$

Compound C-1 where: $a=0–10$, usually between 0 and 3, preferably 1; $R_4$ and $R_5$ are the same or different with each an alkyl group, an alkenyl group, an alkynyl group, or an alkyl, alkenyl, or alkynyl containing acyl group; $R_8$ is an alkyl, alkenyl, or alkynyl group or halogenated alkyl, alkenyl, or alkynyl group, preferably a trifluoromethyl group; $R_{11}$ and $R_{12}$ are the same or different with each an alkyl, alkenyl, or alkynyl group or halogenated alkyl, alkenyl, or alkynyl group; and $X^-$ is an anion, usually a halide, and preferably iodide.

In the general synthesis scheme for Compound C-1 the first step involves reacting the preferably halogenated starting material with (triphenylmethoxy)methyloxirane in the presence of lithium perchlorate in absolute ethanol. A reaction with diethylether in formic acid comprised the second step. The third step is a reaction with an alkyl, alkenyl, or alkynyl halide or an alkyl, alkenyl, or alkynyl containing acyl halide. The general precursor compound is then allowed to react with a selected alkyl, alkenyl, alkynyl or hydroxylated alkyl, alkenyl, alkynyl, halogenated $R_{11}$ and $R_{12}$ that are the same or different with each an alkyl, alkenyl, or alkynyl group or halogenated alkyl, alkenyl, or alkynyl group halide.

With even more specificity, three preferred structures will now be presented with specific synthesis schemes (detailed in the Example section below).

A first specific preferred structure is:

1, DODHP

Specific Synthesis Scheme for DODHP

A second specific preferred structure is:

8, DODMP

Specific Synthesis Scheme for DODMP

-continued

-continued (where R = —CH₂(CH₂)₆CH═CH(CH₂)₇CH₃)

A third specific preferred structure is:

14, DOFEP

There are alternate synthesis pathways for the fluorinated derivatives, two of which are presented below, but other pathways, as with the above synthesis schemes, are considered within the realm of this disclosure.

A First Specific Synthesis Scheme for DOFEP

(where R = —CH₂(CH₂)₆CH═CH(CH₂)₇CH₃)

(where R = —CH₂(CH₂)₆CH═CH(CH₂)₇CH₃)

Compound 17, immediately above, may purchased directly from Aldrich Chemical Company and is usually ordered from this source.

A Second Specific Synthesis Scheme for DOFEP

(where R = —CH₂(CH₂)₆CH═CH(CH₂)₇CH₃)

Note that Compound 19 was prepared from 2,2,2-trifluoroethylamine (Aldrich Chemical Company) according to a literature procedure by Wawzonek, S., McKillip, W., and Peterson, C. J. *Organic Synthesis*, Coil. Vol. V 1973, 758.

General Implications for Synthetic Flexibility

The subject synthesis schemes present opportunities for a widely flexible array of approaches to synthesizing related amine cationic transport molecules. Not only are monosubstituted amine transporters easily synthesized by the subject procedures, but so a disubstituted and trisubstituted derivatives with like or mixed polar domain functional groups readily produced. Either a monosubstituted or disubstituted amine starting material is utilized to generate one or two functional groups in the final compound or during the quaternization step a functional group containing residue is added (see the fluoronated example above).

By way of example and not by way of limitation, a mixed product is synthesized as follows:

wherein $R_{30}$, $R_{40}$, and $R_{50}$ are the same or different and are a hydrogen, alkyl, alkenyl, or alkynyl group, a hydroxy or ether containing alkyl, alkenyl, or alkynyl group, or a halogen containing alkyl, alkenyl, or alkynyl group, $R_{60}$ and $R_{70}$ are carbonyl containing or not containing alkyl, alkenyl, or alkynyl groups, and $X^-$ is a halide (note that the initial starting material functional group or groups may need to be protected via silation or other appropriate means). More specifically, a preferred synthesis scheme for a mixed functional product is:

wherein $R_{60}$ and $R_{70}$ are carbonyl containing or not containing alkyl, alkenyl, or alkynyl groups and $X^-$ is a halide, preferably iodide.

An example of a synthesis that produces a trisubstituted derivative is as follows:

EXAMPLES

Example 1

Synthesis of N,N-[Bis(2-tert-butyldiphenylsilyloxyethyl)] amine Compound 2 in an above Specific Synthesis Scheme To a mixture of diethanolamine (4.78 g, 7.26 mmol), triethylamine (2.5 mL), and 4-dimethylaminopyridine (89 mg, 0.73 mmol) in dichloromethane (73 mL) at 0° C. was added tert-butylchlorodiphenylsilane (5.46 g, 18.14 mmol). On complete addition, the reaction mixture was allowed to warm to room temperature. After 12 h, the reaction mixture was transferred to a separatory funnel and the organic layer was washed successively with saturated aqueous sodium bicarbonate, water, and brine. The organic layer was dried (sodium sulfate), filtered, and the filtrate solvent removed in vacuo. The crude product so obtained was purified by silica gel column chromatography (1% methanol in dichloromethane) to yield 2.53 g (2.13 mmol, 29%) of 2 as an oil. $^1$H NMR (300 MHz, CDCl$_3$) d 7.70–7.34 (m, 20H), 3.79 (t, J=5 Hz, 4H), 2.79 (t, J=5 Hz, 4H), 2.09, (s, 1H), 1.05 (s, 18H); $^{13}$C NMR (75 MHz, CDCl$_3$) d 135.5, 133.6, 129.6, 127.6, 63.5, 51.7, 26.9,19.2; IR (KBr) 3071, 2930,1428 cm$^{-1}$.

Example 2

(±)-[(TriPhenylmethoxy)methyl]oxirane, Compound 3 in an above Specific Synthesis Scheme To a mixture of (±) glycidol (4.00 g, 33.5 mmol), triethylamine (5.7 mL), and 4-dimethylaminopyridine (420 mg, 3.40 mmol) in dichloromethane (170 mL) at 0° C. was added triphenylmethyl chloride (16.5 g, 51.2 mmol). On complete addition, the reaction mixture was allowed to warm to room temperature. After 12 h, the reaction mixture was transferred to a separatory funnel and the organic layer was washed successively with saturated aqueous sodium bicarbonate, water, and brine. The organic layer was dried (sodium sulfate), filtered, and the filtrate solvent removed in vacuo. The crude product so obtained was purified by silica gel column chromatography (3% diethylether in hexane) to yield 8.70 g (27.5 mmol, 82%) of 3 as an oil.$^1$H NMR (300 MHz, CDCl$_3$) d 7.47–7.20 (m, 15H), 3.33–3.30 (m, 1H ), 3.16–3.09 (m, 3H), 2.76 (m, 1H), 2.61 (dd, J=2, 5H,1 H); $^{13}$C NMR (75 MHz, CDCl$_3$) d 143.8,128.6,127.9,127.8, 127.1, 127.0, 86.7, 64.7, 51.0, 44.6; IR (KBr) 3057, 2922, 1448 cm$^{-1}$.

Example 3

(±)-3-[N,N-bis(2-tert butyldiphenylsilyloxyethyl)amino]-1-(Triphenylmethoxy)-2-propanol, Compound 4 in an above Specific Synthesis Scheme To a mixture of (±)-(triphenylmethoxy)methyloxirane (7.66 g, 24.2 mmol) and lithium perchlorate (5.87 g, 55.2 mmol) in absolute ethanol (110 mL) was added amine 2 (11.7 g, 20.2 mmol). The reaction mixture was warmed to 65° C. and allowed to stir for 24 h. After this time, the reaction solution was allowed to cool to room temperature and then transferred to a separatory funnel containing diethylether (100 mL). The resultant mixture was sequentially washed with saturated aqueous sodium bicarbonate, water, and brine. The organic layer was dried over sodium sulfate, filtered and the filtrate was concentrated by rotary evaporation to give the crude product as a yellow oil. Purification was accomplished by SiO$_2$ column chromatography (3% methanol in dichloromethane) to yield 14.5 g (16.1 mmol, 80%) of 4 as an oil. $^1$H NMR (300 MHz, CDCl$_3$) d 7.65–7.20 (m, 25H), 3.73–3.56 (m, 5H), 3.17 (dd, J=5, 9 Hz, 1H), 2.97 (dd, J=5, 9 Hz, 1H), 2.69 (m, 5H), 2.45 (dd, J=10, 12 Hz, 1H ), 1.02 (s, 18H); $^{13}$C NMR (75 MHz, CDCl$_3$)d 144.1, 135.5, 134.7, 133.5, 129.6, 128.7, 128.6, 127.7, 127.6, 126.8, 86.4, 67.2, 66.1, 62.1, 58.4, 56.6, 26.8, 26.5, 19.0; IR (KBr) 3445, 3069, 2930, 1427 cm$^{-1}$.

Example 4
(±)-3-[N,N-Bis(2-tet-butyldiphenylsilyloxyethyl)amino]-1,2-propanediol, Compound 5 in an above Specific Synthesis Scheme To a mixture of amine 4 (8.43 g, 9.40 mmol) in diethylether (12 mL) was added 85% formic acid (35 mL). The resulting reaction mixture was stirred at room temperature for 20 h. After this time, solid $NaHCO_3$ was added to neutralize the acidic solution. The resultant mixture was subsequently diluted with diethylether (100 mL) and transferred to a separatory funnel. The organic layer was separated and sequentially washed with water, and brine. Purification was accomplished by $SiO_2$ column chromatography (3% methanol in dichloromethane) to yield 3.75 g ( 5.73 mmol, 61%) of 5 as an oil. $^1H$ NMR (300 MHz, $CDCl_3$) d 7.65–7.31 (m, 20H), 3.68–3.60 (m, 6H), 3.40 (dd, J=4, 9 Hz, 1H), 2.71 (m, 4H), 2.57 (d, J=7 Hz, 2H), 1.03 (s, 18H); $^{13}C$ NMR (75 MHz, $CDCl_3$) d 135.5, 133.4, 129.7, 127.7, 68.0, 64.4, 62.0, 57.2, 56.7, 26.8, 19.0; IR (KBr) 3432, 3070, 2931, 1428 $cm^{-1}$.

Example 5
(±)-3-[N,N-Bis(2-tert-butyldiphenylsilyloxyethyl)amino]-1,2-bis(9(z)-octadecenoyloxy)propane, Compound 6 in an above Specific Synthesis Scheme To a mixture of diol 5 (4.78 9, 7.26 mmol), triethylamine (2.5 mL), and 4-dimethylaminopyridine (89 mg, 0.73 mmol) in dichloromethane (73 mL) at 0° C. was added dropwise oleoyl chloride (5.46 g, 18.14 mmol). On complete addition, the reaction mixture was allowed to stir at 0° C. for 4 h whereupon an additional portion of dichloromethane (20 mL) was added. The reaction mixture was then transferred to a separatory funnel and the organic layer was washed successively with saturated aqueous sodium bicarbonate, water, and brine. The organic layer was dried (sodium sulfate), filtered, and the filtrate solvent removed in vacuo. The crude product so obtained was purified by silica gel column chromatography (6% EtOAc in Hexane) to yield 2.53 g (2.13 mmol, 29%) of 6 as an oil. $^1H$ NMR (300 MHz, $CDCl_3$) d 7.67–7.34 (m, 20H), 5.37 (m, 4H), 5.03 (m, 1H), 4.29 (dd, J=3, 12 Hz, 1H), 4.06 (dd, J=6, 12 Hz, 1H), 3.65 (t, J=6, 4H), 2.67 (m, 6H), 2.23 (m, 4H), 2.02 (m, 8H), 1.51 (m, 4H), 1.29 (m, 40), 1.05 (s, 18H), 0.90 (t, J=5 Hz, 6H); $^{13}C$ NMR (75 MHz, $CDCl_3$) d 173.3, 172.9, 135.5, 133.6, 130.0, 129.8, 129.7, 129.6, 127.6, 127.5, 70.0, 63.5, 62.5, 57.0, 55.4, 34.3, 34.05, 31.9, 30.0, 29.8, 29.7, 29.5, 29.4, 29.3, 29.2, 29.1 (2), 27.4, 27.2, 27.0, 26.8, 24.9 (2), 22.7, 19.1, 14.1; IR (KBr) 3071, 2927, 1741 $cm^{-1}$.

Example 6
(±)-3-[N,N-Bis(2-hydroxyethyl)amino]-1,2-bis(9(z)-octadecenoyloxy)propane, Compound 7 in an above Specific Synthesis Scheme To a solution of amine 6 (2.50 g, 2.10 mmol) in THF (11 mL) at 0° C. was added dropwise a solution of tetrabutylammonium fluoride ( 6 mL of a 1M solution in THF, 6 mmol). The reaction was stirred at 0° C. for 15 h at which time analysis by thin layer chromatography revealed that no starting material was present. The reaction mixture was diluted with dichloromethane and transferred to a separatory funnel. The reaction mixture was washed sequentially with saturated aqueous sodium bicarbonate, water, and brine. The resultant organic layer was dried over sodium sulfate, filtered and the filtrate solvent removed in vacuo. The crude product was passed through a short column of silica gel using 5% methanol in methylene chloride to yield 1.03 g (1.45 mmol, 69%) of 7 as an oil. $^1H$ NMR (300 MHz, $CDCl_3$) d 5.34 (m, 4H), 5.18 (m, 1H), 4.36 (dd, J =3, 12 Hz, 1), 4.10 (dd, J=6, 12 Hz, 1H), 3.60 (t, J=5 Hz, 4H), 2.71 (m, 6H), 2.32 (dd, J=7, 14 Hz, 4H), 2.00 (m=8H), 1.61 (m, 4H), 1.37–1.15 (m, 40H), 0.87 (t, J=6 Hz, 6H); $^{13}C$ NMR (75 MHz, $CDCl_3$) d 173.7, 173.5, 129.9, 129.7, 129.6, 70.0, 63.5, 59.8, 57.2, 55.8, 34.3, 34.0, 31.9, 29.7 (2), 29.6 (2), 29.5, 29.4, 29.3, 29.1 (2), 27.2, 27.1, 24.8, 22.6, 14.1; IR (KBr) 3416, 2925, 1740 $cm^{-1}$.

Example 7
(±)-N,N-[Bis(2-hydroxyethyl)]-N-methyl-N-[2,3-bis(9(z)-octadecenoyloxy)propyl]ammonium chloride (DODHP), Compound 1 in an above Specific Synthesis Scheme To a sealed tube containing amine 7 (0.40 g, 0.56 mmol) was added iodomethane (3 mL). The tube was flushed with argon then sealed. The reaction mixture was heated to 80° C. for 15 h. After this time, the reaction mixture was concentrated under a stream of argon (Caution: perform evaporation in a fume hood). The resulting yellow oil was dissolved in methylene chloride and transferred to a round bottomed flask. This mixture was concentrated by rotary evaporation to insure that all residual iodomethane was removed. The crude product was passed through a short silica gel column (gradient, 5%–10% methanol in dichloromethane) to yield 0.47 g (0.55 mmol, 98%) of 1 as a wax. $^1H$ NMR (300 MHz, $CDCl_3$) d 5.69 (m, 1H), 5.32 (m, 4H), 4.47 (dd, J=3, 12 Hz, 1H), 4.25–4.12 (m, 5H), 3.95–3.76 (m, 6H), 3.36 (s, 3H), 2.57 (s, 2H), 2.37 (m, 4), 1.99 (m, 8H), 1.58 (m, 4H), 1.37–1.24 (m, 40H), 0.86 (t, J=6 Hz, 6H); $^{13}C$ NMR (75 MHz, $CDCl_3$) d 173.2, 172.7, 129.9, 129.5 (2), 65.5 (2), 63.9, 63.3, 55.6, 51.2, 34.2, 33.9, 31.8, 29.7, 29.5, 29.4, 29.2, 29.1, 29.0 (2), 27.1, 24.7, 24.6, 22.6, 14.0); IR (KBr).

Example 8
(±)-1-(TriPhenylmethoxy)-3-[N,N-bis(2-methoxyethyl)amino]-2-propanol, Compound 10 in an above Specific Synthesis Scheme To a mixture of oxirane 3 (5.00 g, 15.8 mmol) and lithium perchlorate (3.36 g, 31.6 mmol) in absolute ethanol (80 mL) was added amine 9 (2.53 9, 19.0 mmol). The reaction mixture was warmed to 65° C. and allowed to stir for 24 h. After this time, the reaction solution was allowed to cool to room temperature and then transferred to a separatory funnel containing diethylether (20 mL). The resultant mixture was sequentially washed with saturated aqueous sodium bicarbonate, water, and brine. The organic layer was dried over sodium sulfate, filtered and the filtrate was concentrated by rotary evaporation to give the crude product as a yellow oil. Purification was accomplished by $SiO_2$ column chromatography (3% methanol in dichloromethane) to yield 6.46 g (14.18 mmol, 90% ) of 10 as an oil. $^1H$ NMR (300 MHz, $CDCl_3$) d 7.49–7.22 (m, 15H), 3.82 (m, 1H), 3.44 (m, 4H), 3.34 (s, 6H), 3.22 (dd, J=6, 9 Hz, 1H), 3.06 (dd, J=6, 9 Hz, 1H), 2.89–2.71 (m, 5H), 2.57 (dd, J=9, 13 Hz, 1H); $^{13}C$ NMR (75 MHz, $CDCl_3$) d 144.0, 128.7, 127.7, 126.9, 71.2, 67.8, 66.0, 58.7, 58.4, 54.7; IR (KBr) 3437, 3058, 2874, 1449 $cm^{-1}$.

Example 9
(±)-3-[N,N-Bis(2-methoxyethyl)amino]-1,2-propanediol Compound 11 in an above Specific Synthesis Scheme To a mixture of amine 10 (2.86 g, 6.28 mmol) in diethylether (13.4 mL) was added 85% formic acid (16.7 mL). The resulting reaction mixture was stirred at room temperature for 20 h. After this time, $NaHCO_3$ was added to neutralize the acidic solution. The resultant mixture was subsequently diluted with diethylether ( ) and transferred to a separatory funnel. The organic layer was separated and sequentially washed with water, brine, and dried (sodium sulfate). Purification was accomplished by SiO$_2$ column chromatography (3% methanol in dichloromethane) to yield 0.99 9 (4.64 mmol, 74%) of 11 as an oil. $^1$H NMR (300 MHz, CDCl$_3$) d 3.68 (m, 2H), 3.53–3.39 (m, 6H), 3.33 (s, 6H), 2.86–2.70 (m, 5H), 2.64 (d, J=6 Hz, 2H); $^{13}$C NMR (75 MHz, CDCl$_3$) d 71.1, 68.7, 64.7, 58.7, 57.7, 54.8; IR (KBr) 3413, 2876 cm$^{-1}$.

Example 10

(±)-3-[N,N-Bis(2-methoxyethyl)amino]-1,2-bis(9(z)-octadecenoyloxy)propane, Compound 12 in an above Specific Synthesis Scheme To a mixture of diol 11 (0.30 g, 1.41 mmol), triethylamine (0.5 mL), and 4-dimethylaminopyridine (17.2 mg, 0.14 mmol) in dichloromethane (14 mL) at 0° C. was added dropwise oleoyl chloride (1.10 g, 3.66 mmol). On complete addition, the reaction mixture was allowed to stir at 0° C. for 4 h whereupon an additional portion of dichloromethane (10 mL) was added. The reaction mixture was then transferred to a separatory funnel and the organic layer was washed successively with saturated aqueous sodium bicarbonate, water, and brine. The organic layer was dried (sodium sulfate), filtered, and the filtrate solvent removed in vacuo. The crude product so obtained was purified by silica gel column chromatography (1% methanol in dichloromethane) to yield 150 mg (0.21 mmol, 15%) of 12 as an oil. $^1$H NMR (300 MHz, CDCl$_3$) d 5.31 (m, 4H), 5.08 (m, 1H), 4.35 (dd, J =3, 12 Hz, 1), 4.09 (dd, J=6, 12 Hz, 1), 3.40 (t, J=6 Hz, 4H), 3.29 (s, 6H), 2.76–2.68 (m, 6H), 2.26 (m, 4H), 1.98 (m, 8H), 1.58 (m, 4H), 1.35–1.22 (m, 40H), 0.85 (t, J=6 Hz, 6H); $^{13}$C NMR (75 MHz, CDCl$_3$) d 173.3, 173.0, 129.9, 129.6, 71.4, 70.1, 63.7, 58.7, 55.2. 54.8, 34.3, 34.1, 31.8, 29.7, 29.6, 29.5, 29.2, 29.1, 29.0, 27.0 (2), 24.8, 22.6,14.0; IR (KBr) 2925, 2854, 1740 cm$^{-1}$.

Example 11

(±)-N,N-Bis(2-methoxyethyl)-N-methyl-N-[2,3-bis(9(z)-octadecenoyloxy)propyl]ammonium chloride (DODMP), Compound 8 in an above Specific Synthesis Scheme To a sealed tube containing amine 12 (150 mg, 0.20 mmol) was added iodomethane (3 mL). The tube was flushed with argon then sealed. The reaction mixture was heated to 80° C. for 15 h. After this time, the reaction mixture was concentrated under a stream of argon (Caution: perform evaporation in a fume hood). The resulting yellow oil was dissolved in methylene chloride and transferred to a round bottomed flask. This mixture was concentrated by rotary evaporation to insure that all residual iodomethane was removed. The crude product was passed through a short silica gel column (gradient, 5%–10% methanol in dichloromethane) to yield 162 mg (0.19 mmol, 95%) of 8 as a wax. $^1$H NMR (300 MHz, CDCl$_3$) d 5.59 (m, 1H), 5.24 (m, 4H), 4.40 (dd, J=3, 12 Hz, 1H), 4.13–3.75 (m, 11H), 3.34 (m, 9H), 2.25 (m, 4H), 1.91 (m, 8H), 1.51 (m, 4H), 1.27–1.15 (m, 40H), 0.78 (m, 6H); $^{13}$C NMR (75 MHz, CDCl$_3$) d 172.8, 172.6, 129.8, 129.4, 129.4, 65.9 (2), 63.5, 63.2, 63.0, 59.2, 50.4, 34.1, 33.8, 31.7, 29.5 (2), 29.3, 29.2 (2), 29.1, 29.0, 28.9 (2), 29.8, 27.0 (2), 24.5, 24.4, 22.5, 13.9; IR (KBr) 3004, 2925, 1744 cm$^{-1}$.

Example 12

(±)-N-(2,2,2-Trifluoroethyl)-N,N-dimethyl-N-[2,3-bis(9(z)-octadecenoyloxy)gropyl]ammonium chloride (DOFEP), Compound 14 in an above Specific Synthesis Scheme To a sealed tube containing amine 15 (0.50 g, 0.77 mmol) in DMF (5 mL) was added 2-iodo-1,1,1-trifluoroethane (1.1 mL). The tube was flushed with argon then sealed. The reaction mixture was heated to 100° C. for 15 h. After this time, the reaction mixture was transferred round bottom flask and the volatiles (DMF, excess ICH$_2$CF$_3$) were removed via distillation at reduced pressure. The resulting yellow oil was passed through a short silica gel column (gradient, 5%–10% methanol in dichloromethane) to yield 67 mg (0.07 mmol, 10%) of 14 as a solid.$^1$H NMR (300 MHz, CDCl$_3$) d 5.59 (m, 1H), 5.33 (m, 4H), 4.51 (m, 2H), 4.13 (dd, J=6, 12, 1), 3.87 (dd, J=9, 14 Hz, 1), 3.53 (s, 6H), 2.35 (m, 4H), 1.99, (m, 8H), 1.59 (m, 4H), 1.29–1.25 (m, 40H), 0.87 (t, J=7 Hz, 6H);; $^{13}$C NMR (75 MHz, CDCl$_3$) d 173.0, 172.5, 129.9, 129.8, 129.5, 129.4, 66.0, 65.6, 62.8, 54.6, 34.1, 33.8, 31.7, 39.7, 29.6, 29.4 (2), 29.3, 29.1 (2), 29.0 (2), 28.9, 27.1, 27.0, 24.6, 24.5, 22.5, 13.9); IR (KBr).

Example 13

Liposome formulation.

An appropriate mass of the cationic lipid and a neutral lipid (DOPE) were added as solutions in chloroform to 1.9 mL sample vials to yield a 50:50 molar ratio of cationic lipid:neutral lipid. The chloroform was removed via rotary evaporation at 37° C. The resulting thin lipid films were placed under vacuum overnight to insure that all traces of solvent have been removed. The lipid mixture was resuspended in 1 mL sterile water at 70° C. until the film is hydrated, and then vortex mixed to afford an emulsion (unsonicated preparation). These emulsions were formulated at a cationic lipid concentration of 1 mM. To form the sonicated preparations used in this study, the lipid emulsions were sonicated using a Branson sonifier 450 sonicator equipped with a cup horn and recirculating water bath (35° C., 80% output with 2 sec delays over 15 minutes.). By performing comparative transfection experiments, it was determined that sonication of cytofectin emulsions above their phase transition temperature did not significantly alter transfection efficacy. Furthermore, sonication at or above 70° C. resulted in partial lipid decomposition as determined by thin layer chromatography.

Example 14

Cell culture.

NIH 3T3 cells were obtained from ATCC (CRL 1658), cultured in Dulbecco's Modified Eagle's Medium with 10% calf serum, and plated on standard 24 well tissue culture plates 12 to 24 hours prior to transfection. Cells were approximately 80% confluent at the time of transfection. CHO cells (ATCC CCL 61) were cultured using Ham's F12 medium supplemented with 10% fetal calf serum, and plated as described for NIH 3T3.

Example 15

Transfection of cultured cells.

NIH 3T3 cells were plated onto 24 well tissue culture plates as described above. The growth media was removed via aspiration and the cells were washed once with 0.5 mL PBS/well. The liposome/DNA complexes were formed through sequential addition of appropriate amounts of DMEM (serum-free), plasmid DNA (4 micrograms), and the liposome formulation into a 2 mL Eppendorf tube to a total volume of 800 microliters. Typically, 24 microliters of a lipid emulsion (1 mM cytofectin, 1 mM DOPE) were used to complex 4 micrograms of DNA to yield a 2:1 cytofectin to DNA molar charge ratio. The addition of these substances was followed by thorough vortex mixing and incubation for 15 minutes at room temperature. A 200 microliter aliquot of the resultant transfection complex was added to each well (1 microgram DNA/well, n=4) and the is cells were incubated for 4 hrs. at 37° C. At this time, 500 microliters of the appropriate growth media+10% calf serum/well was added and the cells cultured for approximately 48 hours prior to lysis and analysis. The sample transfections were subsequently repeated a minimum of three times for each cell line in order to ensure reproducibility.

Example 16

Intratracheal instillation of DNA or lipid/DNA complexes.

Female Balb/C mice (specific pathogen free) weighing approximately 20 to 21 grams were obtained from Charles River Laboratories. Anesthesia was provided for invasive procedures and animals were terminated by $CO_2$ inhalation in accordance with University of California, Davis guidelines. DNA was prepared for instillation by dilution in sterile water. Lipid/DNA complexes were prepared by mixing 20 micrograms of plasmid DNA (Luciferase) at a 4:1 molar charge ratio (cationic lipid:DNA) in sterile water for injection (total volume of 240 microliters). Mixtures were prepared and vortex mixed at room temperature, and injected within 5 minutes of lipid:DNA complex formation. Neck dissections were performed on anesthetized mice using a 1 cm incision through the skin of the anterior neck, dissection of the salivary gland and musculature surrounding the anterior trachea immediately below the larynx, and instillation of 240 microliters of DNA or lipid/DNA complex using a ½" 30 g needle inserted 1–3 tracheal ring interspaces inferior to the larynx. After injection, the salivary gland was placed over the tracheal defect, and the superficial neck wound closed with staples. Mice were killed 48 hours after treatment and a tracheal/lung block dissected, homogenized in lysis buffer, and assayed for luciferase protein as described below. Mock treated mouse lung/trachea was used for assessment of background luciferase activity. No activity was detected in control mock-treated mouse tissue.

Example 17

Luciferase assay.

Relative luciferase activity was determined by using the Enhanced Luciferase Assay Kit and a Monolight 2010 luminometer (both from Analytical Luminescence Laboratories, San Diego, Cailf.). This was accomplished by directly applying 233.3 mL of concentrated luciferase lysis buffer (final concentration 0.1M potassium phosphate pH 7.8, 1% Triton X-100, 1 mM DTT, 2 mM EDTA) to each well and placing the cells on ice for 15 minutes. Removal of growth media was not necessary prior to the application of the lysis buffer. This technique enhances reproducibility by avoiding the possibility of cell loss during media removal. An analogous experiment where the growth media was removed afforded similar results. Luciferase light emissions from 31 mL of the lysate were measured over a 10 second period, and results were expressed as a function of an assumed total lysate volume of 933.3 mL. Activity has been expressed as relative light units, which are a function of assay conditions, luciferase concentration, luminometer photomultiplier tube sensitivity and background. Under the conditions described above, relative light units are related to luciferase protein mass by the equation [fg luciferase=(RLU/48.6)−824].

Example 18

Transfection Data

Figure 3:
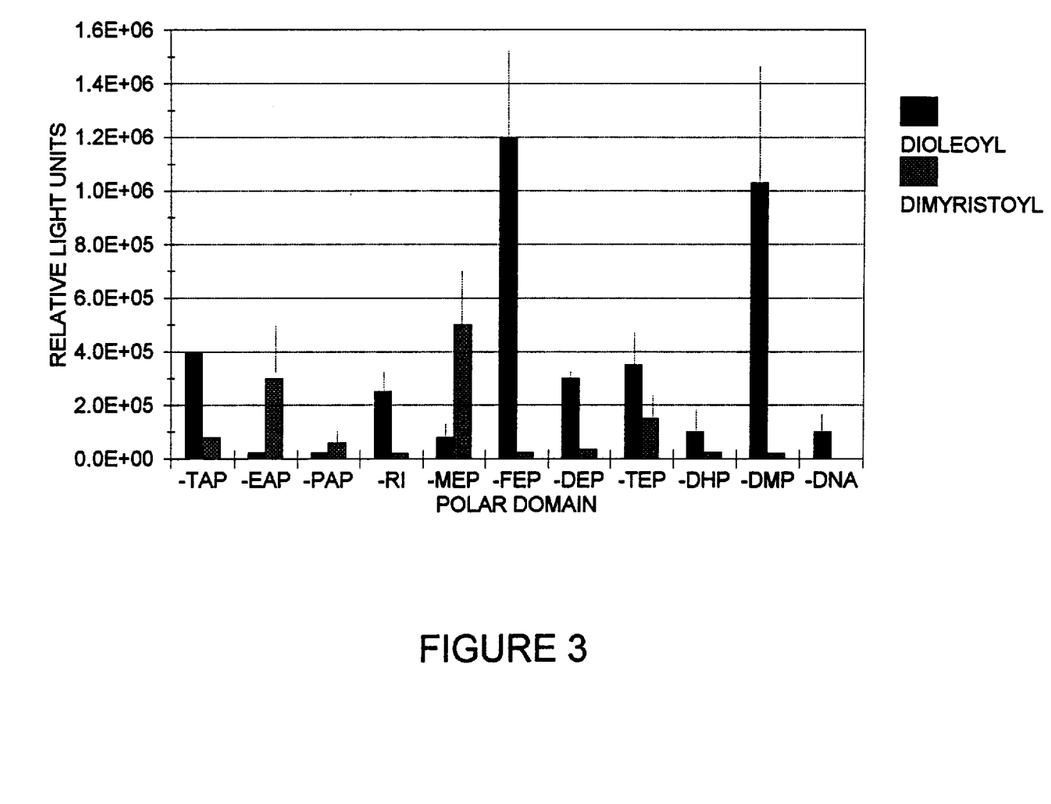
FIG. 3 shows transfection in vivo data for various amine cytofectins.

Interpretation of FIGS. 1–3 is facilitated by reference to the following list of abbreviations, prefixes, or suffixes and the associated structures:

-TAP

-EAP

-PAP

-RI

-MEP

-FEP

-DEP

-TEP

-continued

-DHP

-DMP

DO — as a prefix for the above "R" indicates dioleoyl (with the carbonyl)

DM — as a prefix for the above "R" indicated dimyristoyl (with the carbonyl)

DOPE — Dioleoylphosphatidylethanolamine

DOTMA — N-[1-(2,3-dioleyloxy)propyl]-N,N,N-trimethylammonium bromide [DIETHER]

FIG. 1 shows a comparison of cytofectin-mediated DNA transfection using NIH 3T3 cells. DNA transfections were performed in quadruplicate as described in the experimental procedures using a 2:1 molar charge ratio (lipid charge to DNA phosphate charge). The data demonstrates that the incorporation of a dihydroxyethyl substituted ammonium functionality in the lipid polar domain leads to significantly higher transfection efficacy in vitro. Results are summarized in bar graph form as the mean (n=4) and standard deviation of total luciferase light units (RLU) obtained from cells lysed after transfection of 1 microgram of DNA. All cytofectins were formulated at a 1:1 molar ratio with DOPE.

In FIG. 2 there is shown an in vivo comparison of cytofectin-mediated DNA transfection. Balb-C mice were transfected with plasmid DNA using various cytofectins. Intratracheal instillations of cytofectin:DNA complexes were performed as described in the experimental procedures. The data demonstrates that the incorporation of dimethoxyethyl and triflouroethyl substituted ammonium functionality in the lipid polar domain leads to significantly higher transfection efficacy in vivo. Results are summarized in bar graph form as the mean (n=4) and standard deviation of total luciferase light units (RLU) obtained from trachea/lung blocks lysed 48 hours after treatment with 20 micrograms of DNA.

The transfection activity of various compounds is illustrated in FIG. 3. As can be seen in FIG. 3, the dioleoyl derivatives of -FEP and DMP of the subject invention are exceptionally effective in transfection. General transfection conditions were as above.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. A composition of matter having the structure:

wherein a, b, or d are the same or different and wherein a, b, and d=0–1, $R_4$ and $R_5$ are the same or different with each an alkyl group, an alkenyl group, an alkynyl group, or an alkyl, alkenyl, or alkynyl containing acyl group;

$R_8$ is a hydrogen, an alkyl, alkenyl, or alkynyl group;

$R_9$ is a halogenated alkyl alkenyl, or alkynyl group;

$R_{10}$ is a halogenated alkyl, alkenyl, or alkynyl group; and $X^-$ is an anion.

2. A composition of matter having the structure:

wherein a, b, and d=0—1

$R_4$ and $R_5$ are the same or different with each an alkyl group, an alkenyl group, an alkynyl group, or an alkyl, alkenyl, or alkynyl containing acyl group;

$R_8$ is a hydrogen or methyl group;

$R_9$ and $R_{10}$ are trifluoromethyl groups; and $X^-$ is an anion.

3. A composition of matter having the structure:

wherein a=1, b and d=0

$R_4$ and $R_5$ are the same or different with each an alkyl group, an alkenyl group, an alkynyl group, or an alkyl, alkenyl, or alkynyl containing acyl group;

$R_8$ is a hydrogen or methyl group;

$R_9$ and $R_{10}$ are trifluoromethyl groups; and $X^-$ is an anion.

4. A composition of matter having the structure:

wherein
a=1
$R_4$ and $R_5$ are acyl containing groups,
$R_8$ is a trifluoromethyl group;
$R_{11}$ and $R_{12}$ are methyl groups; and
$X^-$ is an anion.

* * * * *